United States Patent [19]

Zastrow et al.

[11] Patent Number: 5,667,772
[45] Date of Patent: Sep. 16, 1997

[54] PREPARATION CONTAINING A FLUOROCARBON EMULSION AND USABLE AS COSMETICS OR DERMATICS

[75] Inventors: Leonhard Zastrow, Wiesbaden; Klaus Stanzl, Waldesch; Joachim Röding, Wiesbaden, all of Germany

[73] Assignee: Lancaster Group AG, Ludwigshafen, Germany

[21] Appl. No.: 654,026

[22] Filed: May 28, 1996

Related U.S. Application Data

[63] Continuation of Ser. No. 256,180, filed as PCT/EP93/02751 published as WO94/09754 May 11, 1994, abandoned.

[30] Foreign Application Priority Data

Oct. 29, 1992 [DE] Germany .............. 42 366 070

[51] Int. Cl.$^6$ .................................................. A61K 7/48
[52] U.S. Cl. ............... 424/18.02; 424/47; 424/59; 424/65; 424/70.1; 424/70.7; 424/75; 424/401; 424/78.03; 514/844; 514/845; 514/846; 514/847; 514/944; 514/945
[58] Field of Search .................. 424/401, 47, 59, 424/69, 65, 70.1, 70.7, 73, 78.02, 78.03; 514/844, 845, 846, 847, 944, 945

[56] References Cited

U.S. PATENT DOCUMENTS 5,275,808  1/1994  Murray et al. .............. 424/70

FOREIGN PATENT DOCUMENTS 2534315  2/1976  Germany .
9100110  1/1991  WIPO .

*Primary Examiner*—Jyothsan Venkat
*Attorney, Agent, or Firm*—Collard & Roe, P.C.

[57] ABSTRACT

The invention relates to preparations for the improved release of oxygen into the skin and to the use of same as cosmetics/dermatics. The preparations according to this invention contain, as the essential component, fluorocarbon emulsions consisting of nonionic emulsifiers and an oxygen-loaded fluorocarbon or fluorocarbon mixture, the fluorocarbon content being in the range from 0.05 to 100% by weight/volume. They are prepared by emulsifying the corresponding components and incorporating the resulting emulsion in known carriers for, for example, ointments, creams, lotions, waters, alcoholic extracts, pastes, powders, gels, tinctures or masks.

3 Claims, No Drawings

PREPARATION CONTAINING A FLUOROCARBON EMULSION AND USABLE AS COSMETICS OR DERMATICS

This is a continuation of application(s) Ser. No. 08/256, 180 filed on Jun. 28, 1994 now abandoned which is a 371 of International Application PCT/EP93/0271 filed on Oct. 7, 1993 published as WO94/09754 May 11, 1994 and which designated the U.S.

The invention relates to cosmetic and dermatological preparations which are efficient in improving the oxygen supply to the skin.

To improve supply of oxygen to the skin, it has already been proposed to use peroxides, such as hydrogen peroxide, in order to stimulate the cell metabolism of the skin via the nascent oxygen formed. However, the considerable side effects, such as skin irritations, have prevented their use. DE-A-2,534,315 claims an $O_2$-containing cosmetological formulation composed of an $O_2$-saturated gaseous fluorocarbon and a surfactant in aqueous phase in an aerosol container. Borgarello (EP-A-296,661) has developed an isotropic single-phase system for the cosmetic sector in which halogenated compounds are supposed to act as oxygen carriers. A typical composition consists of 34% of a mixture of. perchloro-1-butyltetrahydrofuran and polyfluoro-1-propyl-tetrahydrofuran, 7% of isopropanol, 49% of water and 10% of emulsifier. The emulsifiers used are highly surface-active fluorine surfactants, for example of the perfluoroalkanesulfonamide type, which are known to be extremely toxic on i.p. application in mice (LD50 0.1 to 0.2 g/kg) and also act as an irritant on the skin. Further possible solutions relate to the use of a haemolymph extract from crustaceans or of an extract of proteins and proteids from bovine spleen. Human haemoglobin or, more recently, haemoglobin prepared by biotechnology has hitherto not been available in a form utilizable for topical purposes. Furthermore, it is known that PO/EO block polymers having EO contents of up to 50% have relatively good solubility for gaseous oxygen. In contrast, block polymers having EO contents of 60 to 80% are solid products exhibiting low solubility for oxygen.

However, so far no convincing and physically detectable toning and reviving of the skin surface could be achieved by means of the preparations and methods mentioned.

The object of the invention is to improve the oxygen supply to the skin by means of a specific preparation based on a suitable emulsion of fluorocarbons in such a manner that a detectable effect is achieved.

According to the invention, the preparation consists of an aqueous emulsion having a nonionic surfactant content of 1 to 8% by weight as the emulsifier and an oxygen-loaded fluorocarbon or fluorocarbon mixture content, the fluorocarbon content being in the range from 0.02 to 100% w/v (w/v=weight/volume) in a carrier suitable for the application.

The preparation according to the invention can be present, depending on the specific method of application, in solid, liquid or semi-liquid form, for example as powder, lotion, shampoo, cream or gel paste. The carriers suitable for each of these forms are known to one skilled in the art.

The essential feature of the invention is the presence of the fluorocarbon emulsion in the preparations, which ensures efficient toning of the skin. Particularly preferred fluorocarbons are perfluorodecaline, F-butyltetrahydrofuran, perfluorotributylamine, perfluorooctyl bromide, bis(fluorobutyl)ethene or bis(fluorohexyl)ethene or $C_6$-$C_9$-perfluoroalkane.

The fluorocarbon content in the emulsion is in the range from 20 to 100% by weight/volume, preferably in the range from 40 to 100% by weight/volume. A particularly preferred range is that from 70 to 100% by weight/volume.

The term "fluorocarbons" used here is understood to mean perfluorinated or highly fluorinated carbon compounds or mixtures capable of transporting gases, such as $O_2$ and $CO_2$. Highly fluorinated hydrocarbon compounds for the purposes of this invention are those in which most hydrogen atoms have been replaced by fluorine atoms. In most cases, this is achieved if about up to 90% of the hydrogen atoms have been replaced by fluorine atoms. Preferred fluorocarbons for the purposes of the present invention are those in which at least 95% of the hydrogen atom have been replaced, 98% being more preferred and 100% being most preferred.

Suitable emulsifiers are nonionic surfactants, such as emulsifiers of the EO/PO block polymer type and/or ethoxylated sorbitan fatty acid esters, fluorinated nonionic surfactants according to DD-WP131,555 or perfluorinated iminobis(polyoxyalkylene) according to DD-WP265,398 A1.

These fluorocarbon emulsions can be prepared by DD-WP222,494 A1 or another known method ("Tenside Surfactants Detergents", 25 (1989), 5, p. 284). The auxiliary emulsifiers used include alkali metal salts of long-chain fatty acids and phospholipids.

The advantage of the preparations according to the invention containing a fluorocarbon emulsion when used as cosmetics or dermatics is that an additional oxygen supply imparted by the fluorocarbon promotes circulation and thus the metabolic processes in the epidermal layer and activates the general state of transpiration. The increased cell respiration strengthens the natural skin defence potential and promotes elimination of skin toxins.

In contrast to the known preparations mentioned at the beginning, the preparations according to the invention demonstrate that owing to their extraordinarily high dissolving power for oxygen, the chemically inert fluorocarbons are capable of supplying the skin advantageously with oxygen in topical application.

The use as a cosmetic is not limited to parts of the human face but applies to all epidermal regions of the body, including cellulitis-affected fat tissue with a poor supply and the region of the scalp. Topical application of cosmetics or dermatics containing a fluorocarbon emulsion was previously unknown. Fluorocarbons themselves are chemically and biologically inert organic liquids having a high dissolving power for oxygen. Owing to these characteristics, they have been proposed as gas carriers in blood substitute emulsions and have also been used in humans (K. C. Lowe: "Blood substitutes", Ellis-Horwood, Chichester, GB, 1988).

Depending on the intended specific purpose, the fluorocarbons can be selected in accordance with $O_2$ solubility, partial vapour pressure and lipid solubility. The critical solubility temperature (CST) of the fluorocarbons in n-hexane correlates with their solubility in lipids, for example cell membranes, and is thus a measure of the rate of release through the skin. Thus, for example, perfluorodecaline and perfluorooctyl bromide which have small CST values are released fairly rapidly, while, on the other hand, F-tributylamine which has a high CST value of 59° C. also exhibit a long half life of release. It has been found that fluorocarbons behave ideally upon mixing, and the CST values of such mixtures show a linear relationship with composition. By mixing various fluorocarbons, it is thus possible to establish defined CST values which often cannot be achieved by individual compounds. This finding makes it possible to use fluorocarbon mixtures selectively in order to positively affect the rate of penetration of the skin and their residence time.

Incorporation of the fluorocarbon emulsion as active component in ointments, creams, lotions and other aqueous or alcoholic cosmetic formulations is carried out as a function of the intended purpose, it being possible for the fluorocarbon content and thus the $O_2$ availability to be varied within wide limits. Before incorporation in any cosmetic systems, such as, for example, gels, pastes, powders, ointments, creams, lotions and waters or alcoholic extracts, the emulsion can be partially loaded or saturated with gaseous oxygen. Saturation with atmospheric oxygen already ensures a higher oxygen capacity than any comparable known systems by virtue of the equilibrium which is usually established in accordance with Henry's law.

According to the invention, the fluorocarbon emulsion content in the cosmetic or dermatological preparations can be in the range from 0.05 to 80% by weight, preferably in the range from 0.05 to 60% by weight, and in particular in the range from 1 to 50% by weight.

The invention will now be illustrated in more detail by way of example. Incorporation of the emulsions prepared by DD-WP 494 A1 or another known method takes place without difficulties as shown in Example 1.

Examples I to III below describe the preparation of fluorocarbon emulsions, which are then used in the preparations of Examples 1 to 17.

Exemplary embodiment I

40% of a mixture, ⅔ of which are fluorocarbons, i.e. a mixture of 20% of tetrafluoroethylene and 80% of perfluorotripropylamine, whose boiling range is between 140° and 180° C., and ⅓ of which is the emulsifier polyoxyethylene/propylene copolymer of molecular weight 8000 to 9000, is added to 60% of distilled water with flushing of pure oxygen (0.2 to 0.5 bar), and the mixture is emulsified at an optimum temperature of 7° to 15° C. This can be effected by using any homogenizer having a minimum rotational speed of 10,000 rpm.

To sterilize the oxygen-loaded emulsion, 5 to 10% of ethanol or suitable preservatives are added.

The desired particle size depends on the homogenization time. In this example, it is 15 min., resulting in a particle size of 300 to 500 nm.

Exemplary embodiment II

25% of a perfluoroalkane mixture in the boiling range between 100° and 140° C., consisting of equal amounts of tetrafluoroethylene and perfluorotripropylamine, are slowly mixed with 8.4% of sorbitan fatty acid ester at a temperature of 5° to 20° C. with flushing with pure oxygen (0.2 to 0.5 bar). (The percentages given are based on the content of the finished emulsion.)

The remaining 66.6% consists of distilled water, which is added to the perfluoroalkane/sorbitan fatty acid ester mixture by applying high mechanical shearing forces (12,000 to 15,000 rpm).

This gives an oxygen-loaded emulsion, which, after a homogenization time of 20 minutes, has a particle size of 200 to 400 nm.

Exemplary embodiment III

23% of a perfluoroalkane mixture in the boiling range 170 to 180° C., consisting of 40% of tetrafluoro-ethylene and 60% of perfluorotripropylamine, and 3% of propylene glycol, molecular weight 2000 to 5000 are premixed with flushing with pure oxygen (0.2 to 0.5 bar). (The percentages given are based on the content of the finished emulsion.)

The remaining 74% of distilled water are distributed therein by means of an ultrasound disintegrator (syntrode diameter 20 mm, frequency 50, 40 Hz). Within 2 to 5 minutes, a homogeneous, oxygen-enriched emulsion whose particle size is between 50 and 200 nm, is obtained. The temperature must be between 10° and 25° C.

Example 1

Cream for day and night

| Phase A | |
|---|---|
| Sorbitan sesquioleate | 6.5% |
| Cetyl alcohol, stearyl alcohol (about 50:50 mixture) | 4.0% |
| Isooctyl stearate | 3.0% |
| Phase B | |
| Propylene glycol | 2.1% |
| Allantoin | 0.5% |
| Aloe Vera | 2.0% |
| Benzoic acid | 0.4% |
| Water | qs |
| Phase C | |
| Perfume oil | 1.0% |
| Fluorocarbon emulsion according to Example I | 25.0% |

Preparation

Phase A is heated to 65° C. with stirring. Phase B is also heated to 65° C. and added to Phase A as soon as temperature stability is reached. The homogenization time is 10 minutes. This is followed by the cooling phase. As soon as the temperature of <35° C. is reached, the fluorocarbon emulsion and the perfume oil (Phase C) are added with very slow stirring.

Example 2

Body lotion

| Polyacrylic acid (mol. weight 4 million) | 0.5% |
|---|---|
| Triethanolamine (TEA) | 0.5% |
| Cetyl alcohol, stearyl alcohol (about 50:50 mixture) | 1.5% |
| Propylene glycol | 2.5% |
| Glycerol | 1.5% |
| Aloe Vera | 1.0% |
| Allantoin | 0.5% |
| Fluorocarbon emulsion according to Example I | 15.0% |
| Perfume | 0.5% |
| Water | qs |

The preparation is analogous to Example 1.

Example 3

Cleansing milk

| Phosphoric ester/isopropyl palmitate (ratio 1:1) | 7.5% |
|---|---|
| Polyglycerol ester/isopropyl | 8.5% |

-continued

| | |
|---|---|
| palmitate (ratio 1:1) | |
| Glycerol | 5.0% |
| Panthenol | 2.0% |
| Benzoic acid | 0.5% |
| Perfume | 0.5% |
| Fluorocarbon emulsion according to Example I | 50.0% |
| Deionized water | qs |

The preparation is analogous to Example 1.

Example 4

Face mask

| | |
|---|---|
| Phosphoric ester/isopropyl palmitate (ratio 1:1) | 5.0% |
| Polyoxyethylene sorbitan monolaurate | 8.5% |
| Vitamin E | 0.5% |
| Glycerol | 3.5% |
| Magnesium sulphate | 0.5% |
| Marigold extract | 5.0% |
| Perfume | 0.5% |
| Fluorocarbon emulsion according to Example I | 60.0% |
| Water | qs |

The preparation is analogous to Example 1.

Example 5

Liquid gel

| | |
|---|---|
| Polyacrylic acid (mol. weight 4 million) | 1.0% |
| Hydroxyethylcellulose | 0.2% |
| Polypropylene glycol | 5.0% |
| TEA | 0.5% |
| Vitamin B | 2.0% |
| Fluorocarbon emulsion according to Example II | 45.0% |
| Benzoic acid | 0.3% |
| Perfume | 0.2% |
| Water | qs |

Preparation:
The fluorocarbon emulsion is admixed to the gel at room temperature with slow stirring.

Example 6

Sun preparation

| | |
|---|---|
| Emulsifier system consisting of: Liquid paraffin, polyglycerol ester, stabilizers, isopropyl palmitate, bees wax in approximately equal amounts | 29.5% |
| Glycerol | 3.5% |
| MgSO$_4$.7H$_2$O | 0.5% |
| Vitamin E | 1.5% |
| Aloe Vera | 1.0% |
| Preservative | 0.2% |
| Perfume | 0.5% |
| Fluorocarbon emulsion according to Example II | 5.0% |
| Water | qs |

The preparation is analogous to Example 1.

Example 7

Shower gel

| | |
|---|---|
| Sodium lauryl ether sulphate | 37.0% |
| Magnesium lauryl ether sulphate | 10.0% |
| Pearl lustre concentrate | 3.0% |
| Citric acid | 0.5% |
| Fluorocarbon emulsion according to Example II | 2.5% |
| Perfume | 1.0% |
| Water | qs |

Preparation:
The fluorocarbon emulsion is slowly added to the finished shower bath and stirred therein until a homogeneous mixture is obtained.

Example 8

Shampoo

| | |
|---|---|
| Sodium lauryl ether sulphate | 30.0% |
| Magnesium lauryl ether sulphate | 8.0% |
| Pearl lustre concentrate | 5.0% |
| Alkylamidosulphosuccinate | 3.0% |
| Vitamin B | 1.0% |
| Protein hydrolysate | 1.0% |
| Benzoic acid | 0.2% |
| Citric acid | 0.05% |
| Fluorocarbon emulsion according to Example II | 5.0% |
| Perfume | 0.5% |
| Water | qs |

The preparation is analogous to Example 7.

Example 9

Hair conditioner

| | |
|---|---|
| Cetyl alcohol/stearyl alcohol about 50:50 mixture | 12.0% |
| Isononanoates of the above alcohol mixture | 1.0% |
| Coconut glycerides | 3.5%< |
| Diethylenetricaseinamide | 2.0% |
| Stearic acid | 6.0% |
| Glycerol | 10.0% |
| Citric acid | 0.05% |
| Lecithin | 1.0% |
| Fluorocarbon emulsion according to Example II | 10.0% |
| Water | qs |

The preparation is analogous to Example 1.

Example 10

Roll-on deodorant with a skin-care action

| | |
|---|---|
| Phase A | |
| Emulsifier system consisting of: Liquid paraffin, isopropyl palmitate, phosphoric ester in approximately equal amounts | 18.0% |
| Phase B | |
| Glycerol | 3.0% |

-continued

| | |
|---|---|
| 96 percent strength ethanol | 25.0% |
| Benzoic acid | 0.3% |
| Perfume | 1.5% |
| Water | qs |
| Phase C | |
| Fluorocarbon emulsion according to Example II | 3.5% |

Preparation

First, Phase A is introduced into the mixer at room temperature.

Phase B is then added in portions with rapid stirring, and the mixture is dispersed until homogeneity is reached.

Phase C is slowly stirred in.

Example 11

Aftershave balm

| | |
|---|---|
| Polyacrylic acid (mol. weight 4 million) | 0.5% |
| TEA | 0.5% |
| Glycerol | 1.5% |
| Lanolin | 1.0% |
| Jojoba oil | 1.5% |
| Babassa oil | 1.0% |
| 98% strength ethanol | 10.0% |
| Fluorocarbon emulsion according to Example III | 7.5% |
| Preservatives | 0.4% |
| Perfume | 1.0% |
| Water | qs |

The preparation is analogous to Example 1.

Example 12

Foundation, liquid

| | |
|---|---|
| Emulsifier system consisting of: Glyceryl stearate, $CH_3(CH_2)_{14}CH_2(OCH_2CH_2)_{12}OH$, $CH_3(CH_2)_{14}CH_2(OCH_2)_{20}OH$, cetyl alcohol/stearyl alcohol (about 50:50 mixture), cetyl palmitate in approximately equal amounts | 8.5% |
| Glycerol | 1.5% |
| Propylene glycol | 2.0% |
| Aloe vera extract | 2.5% |
| Benzoic acid | 0.3% |
| Colour combination consisting of: | 3.5% |
| White colorant | 1.00% |
| Black colorant | 0.35% |
| Red colorant | 0.85% |
| Ochre colorant | 1.30% |
| Fluorocarbon emulsion according to Example III | 20.0% |
| Perfume | 0.8% |
| Water | qs |

The preparation is analogous to Example 1.

Example 13

Translucent make-up powder, compact powder

| | |
|---|---|
| Talc | qs |
| Microfibre | 10.0% |
| pearl lustre pigment | 10.0% |
| Magnesium stearate | 9.5% |
| Colour combination consisting of: | 2.6% |
| Brown colorant | 0.8% |
| Black colorant | 0.1% |
| White colorant | 1.2% |
| Red colorant | 0.5% |
| Perfume | 0.5% |
| Binder emulsion | 7.5% |
| Cetyl alcohol/stearyl alcohol (about 50:50 mixture) | 3.5% |
| Propylene glycol | 4.0% |
| Fluorocarbon emulsion according to Example III | 1.5% |
| Water | qs |

Binder emulsion as process promotor

The preparation of the binder is analogous to Example 1.

Example 14

Eye make-up containing sunscreen factor

| | |
|---|---|
| Polyacrylic acid (mol. weight 4 million) | 0.5% |
| TEA | 0.5% |
| Sorbitol | 4.0% |
| Cetyl alcohol/stearyl alcohol (about 50:50 mixture) | 3.5% |
| Paraffin oil | 2.0% |
| Propylene glycol | 1.5% |
| Fluorocarbon emulsion according to Example III | 0.5% |
| Colour combination consisting of: | 4.5% |
| White colorant | 2.0% |
| Brown colorant | 0.5% |
| Black colorant | 0.3% |
| Red colorant | 1.7% |
| Deionized water | qs |

The preparation is analogous to Example 1.

Example 15

Blusher, compacted

| | |
|---|---|
| Talc | qs |
| Silk protein | 5.0% |
| Pearl lustre pigment | 10.0% |
| Magnesium stearate | 5.0% |
| Perfume | 0.5% |
| Binder emulsion | 7.0% |
| Cetyl alcohol/stearyl alcohol (about 50:50 mixture) | 3.5% |
| Propylene glycol | 4.0% |
| Fluorocarbon emulsion according to Example III | 0.5% |
| Deionized water | qs |

Binder emulsion as process promotor.

The preparation of the binder is analogous to Example 1

Example 16

Self-tanning agent

| | |
|---|---|
| Cetyl alcohol/stearyl alcohol (about 50:50 mixture) | 20.0% |
| Glycerol | 5.0% |
| Propylene glycol | 3.0% |
| Dihydroxyacetone | 3.0% |
| Fluorocarbon emulsion according to Example III | 12.5% |
| Perfume | 1.0% |
| Deionized water | qs |

The preparation is analogous to Example 1.

Example 17

Liquid gel

| | |
|---|---|
| Polyacrylic acid (mol. weight 4 million) | 1.0% |
| Hydroxyethylcellulose | 0.2% |
| Propylene glycol | 5.0% |
| TEA | 0.5% |
| Fluorocarbon emulsion according to Example III | 45.0% |
| Preservatives | 0.3% |
| Perfume | 0.2% |
| Water | qs |

Preparation:

The fluorocarbon emulsion is admixed to the gel at room temperature with slow stirring.

We claim:

1. Carrier-based cosmetic preparation containing a fluorocarbon emulsion consisting of a preparation selected from the group consisting of a powder, a lotion, a shampoo, a cream and a gel paste, containing an aqueous emulsion consisting of (i) 1–8% by weight of an nonionic surfactant as the emulsifier, said nonionic surfactant selected from the group consisting of fluorinated iminobis (polyoxyalkylenes), polyoxyethylene/polyoxypropylene copolymers, ethoxylated fluorine surfactants and ethoxylated polypropylene glycols, and (ii) an oxygen-loaded fluorocarbon or fluorocarbon mixture, having at least one fluorocarbon selected from the group consisting of perfluorodecaline, $C_6$–$C_9$-perfluoroalkanes, F-butyltetrahydrofuran, perfluorotributylamine, bis(fluorobutyl)ethene, perfluorooctyl bromide, tetrafluoroethylene, and mixtures thereof, and being capable of dissolving and transporting oxygen to epidermal regions with a topical application thereof;

the fluorocarbon content being in the range from 40% to 100% w/v (weight/volume); and the content of the emulsion in the preparation is in the range of 1% to 50% by weight.

2. A carrier-based cosmetic preparation containing a fluorocarbon emulsion, being a cleansing milk consisting of 7.5% by weight of phosphoric ester/isopropyl palmitate (ratio 1:1);

8.5% by weight of polyglycerol ester/isopropyl palmitate (ratio 1:1);

5.0% by weight of glycerol;

2.0% by weight of panthenol;

0.5% by weight of benzoic acid;

0.5% by weight of perfume;

50% by weight of fluorocarbon emulsion; and qs deionized water; and wherein said fluorocarbon emulsion consists of 40% of a mixture, ⅔ of which is a mixture of 20% of tetrafluoroethylene and 80% of perfluorotripropylamine, whose boiling range is between 140° C. and 180° C., and ⅓ of which is the emulsifier polyoxyethylene/propylene copolymer of molecular weight 8000 to 9000, added to 60% of distilled water with flushing of pure oxygen (0.2 to 0.5 bar).

3. A carrier-based cosmetic preparation containing a fluorocarbon emulsion, being a face mask, consisting of 5.0% by weight of phosphoric ester/isopropyl palmitate (ratio 1:1);

8.5% by weight of polyoxyethylene sorbitan monolaurate;

0.5% by weight of vitamin E;

3.5% by weight of glycerol;

0.5% by weight of magnesium sulphate;

5.0% by weight of marigold extract;

0.5% by weight of perfume;

60.0% by weight of fluorocarbon emulsion; and qs water; and wherein said fluorocarbon emulsion consists of 40% of a mixture, ⅔ of which is a mixture of 20% of tetrafluoroethylene and 80% of perfluorotripropylamine, whose boiling range is between 140° C. and 180° C., and ⅓ of which is the emulsifier polyoxyethylene/propylene copolymer of molecular weight 8000 to 9000, added to 60% of distilled water with flushing of pure oxygen (0.2 to 0.5 bar).

* * * * *